United States Patent
Wardle et al.

[11] Patent Number: 6,107,483
[45] Date of Patent: Aug. 22, 2000

[54] PROCESS FOR THE LARGE-SCALE SYNTHESIS OF 4,10-DINITRO-2,6,8-12-TETRAOXA-4,10-DIAZATETRACYCLO-[5.5.0.05,903,11]-DODECANE

[75] Inventors: Robert B. Wardle, Logan; Robert M. Hajik, Willard; Jerald C. Hinshaw; Thomas K. Highsmith, both of Ogden, all of Utah

[73] Assignee: Cordant Technologies Inc., Salt Lake City, Utah

[21] Appl. No.: 09/362,083

[22] Filed: Jul. 28, 1999

Related U.S. Application Data

[60] Provisional application No. 60/094,848, Jul. 31, 1998.

[51] Int. Cl.⁷ .................................................. C07D 267/02
[52] U.S. Cl. ............................................... 540/546
[58] Field of Search .............................................. 540/546

[56] References Cited

U.S. PATENT DOCUMENTS

| | | |
|---|---|---|
| 3,111,522 | 11/1963 | Vail et al. . |
| 3,356,679 | 12/1967 | Fort et al. . |
| 3,365,454 | 1/1968 | Ferguson et al. . |
| 3,365,455 | 1/1968 | Fort et al. . |
| 3,369,020 | 2/1968 | Ferguson et al. . |
| 3,579,536 | 5/1971 | Vail et al. . |
| 4,487,938 | 12/1984 | Boileau et al. . |
| 5,468,313 | 11/1995 | Wallace, II et al. . |
| 5,498,711 | 3/1996 | Highsmith et al. . |
| 5,529,649 | 6/1996 | Lund et al. . |
| 5,587,553 | 12/1996 | Braithwaite et al. . |
| 5,739,325 | 4/1998 | Wardle et al. . |
| 5,759,458 | 6/1999 | Haaland et al. . |

OTHER PUBLICATIONS

Ramakrishnan and Boyer, "4,10–Dinitro–2,6,8,12–Tetraoxa–4,10–Diazatricyclo[$5.5.0.0^{5,9}0^{3,11}$]–dodecane," Heterocycles vol. 31, pp. 479–481 (1989).

*Primary Examiner*—Deborah C. Lambkin
*Attorney, Agent, or Firm*—Pillsbury Madison & Sutro LLP

[57] ABSTRACT

A process for synthesizing 4,10-dinitro-2,6,8,12-tetraoxa-4,10-diazatetracyclo-[$5.5.0.0^{5,9}0^{3,11}$]-dodecane ("TEX") involves combining at least one hexa-substituted piperazine derivative with a medium containing at least one nitronium anion source and at least one acid sufficiently strong to generate nitronium anions from the nitronium anion source. According to this invention, TEX yield is significantly improved by pre-heating the medium to 55° C. to about 70° C. and maintaining the medium from 55° C. to about 70° C. to permit the hexa-substituted piperazine derivative and nitronium anions to react and form the TEX. At least one $NO_x$ scavenger is added to the medium, preferably before the addition of the hexa-substituted piperazine derivative, to increase TEX yield.

21 Claims, No Drawings

PROCESS FOR THE LARGE-SCALE SYNTHESIS OF 4,10-DINITRO-2,6,8-12-TETRAOXA-4,10-DIAZATETRACYCLO-[5.5.0.0$^{5,9}$0$^{3,11}$]-DODECANE

Priority is claimed on U.S. Provisional Application No. 60/094,848 filed on Jul. 31, 1998, the complete disclosure of which is incorporated herein by reference.

BACKGROUND OF THE INVENTION

1. Field of the Invention

This invention relates to a novel process of making the low sensitivity, high energy and density solid oxidizer 4,10-dinitro-2,6,8,12-tetraoxa-4,10-diazatetracyclo [5.5.0.0$^{5,9}$0$^{3,11}$]-dodecane, also known as "TEX". The process provides several advantages over known processes, including faster reaction times with excellent yields and product purity, making it particularly suitable for large-scale synthesis.

2. Description of the Related Art

The small-scale synthesis of TEX is reported by Boyer et al. in *Heterocycles*, Vol. 31, No. 3, pp. 479–489 (1990), the complete disclosure of which is incorporated herein by reference. Boyer's process starts with 2,3,5,6-tetrahydroxy-1,4-diformylpiperazine (hereinafter referred to as THDFP) and trimeric glyoxal (dihydrate) added to a 0° C. concentrated sulfuric acid medium, which is stirred and maintained at 10° C. to 15° C. for 5 hours. The reaction mixture is then cooled back down to 0° C., and 100% nitric acid is added dropwise, generating an exothermic reaction. Stirring is resumed for 2 hours while the temperature of the reaction mixture is maintained by cooling at between 0° C. to 10° C. The mixture is then allowed to warm to about 25° C. and stirred for another 45 hours. The mixture is then poured onto ice, and a colorless solid precipitate is collected and washed to give a crude mixture which contains TEX.

Boyer et al. reports that the reaction proceeds in the following manner:

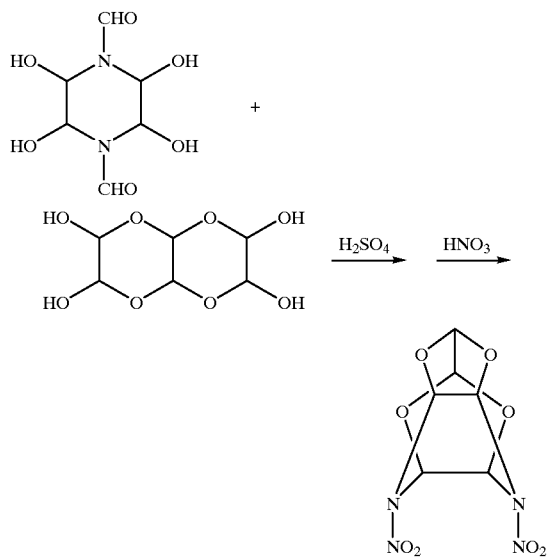

However, the present inventors found that treatment of the THDFP with acid generates monomeric glyoxal equivalent due to decomposition of the THDFP. Not only is the addition of extra amounts of trimeric glyoxal reactant unnecessary, but the present inventors surmised that the additional trimeric glyoxal decomposed in the acid bath to contaminate the final product. As a result, the Boyer et al. process provides low yields of TEX and impure TEX, thus requiring additional purification steps and making the Boyer et al. process unsuitable for scale-up.

Another synthesis route for preparing TEX is disclosed in U.S. Pat. No. 5,498,711, the complete disclosure of which is incorporated herein by reference. According to the '711 patent, TEX is synthesized by reacting 1,4-diformyl-2,3,5,6-tetrahydroxypiperazine and derivatives thereof with a strong acid and a nitrate source. The strong acid and nitrate source of preference are sulfuric acid and nitric acid, respectively. The reaction is exothermic and is allowed to continue for two to three hours. The mixture is then poured onto ice, and a solid precipitate is isolated and washed to give a mixture which contains the TEX.

Although the '711 patent teaches that the reaction can be conducted in the range of from about 50° C. to about 70° C. in temperature, it generally encourages starting the reaction in a bath below this temperature range (with a minor exception in Example 24, which starts the reaction below 55° C.), since the reaction between the hexa-substituted piperazine derivative and the constituents of the concentrated acid medium is exothermic nature. However, it has been discovered by the present inventors that the practice of a decreased temperature at the early stages of the reaction is responsible for relatively low yields of TEX and for the generation of large amounts of NO$_x$ fume off, thus making the reaction more violent and dangerous.

There exists a need for a TEX synthesis procedure which safely controls the exothermic nature of the reaction, which yields TEX in a purity suitable for use in explosive compositions without further purification, and which increases the yield of the TEX obtained.

SUMMARY OF THE INVENTION

It is, therefore, an object of this invention to address a need in the art by providing a method by which 4,10-dinitro-2,6,8,12-tetraoxa-4,10-diazatetracyclo[5.5.0.0$^{5,9}$0$^{3,11}$]-dodecane (herein referred to as TEX) can be synthesized at a sufficiently high purity and yield to permit its large scale production in an economically feasible manner.

In accordance with the objects of this invention, these and other objects are accomplished by the provision of process in which TEX is prepared by combining at least one hexa-substituted piperazine derivative with a medium (also referred to herein as a "bath") comprising at least one nitronium anion source and at least one acid sufficiently strong to generate nitronium anions from the nitronium anion source. At the time the piperazine derivative is combined with the medium, the medium is in a range from about 55° C. to about 70° C. in temperature, preferably from about 55° C. to about 60° C. This temperature range of from about 55° C. to about 70° C. (preferably about 55° C. to about 65° C.) is maintained during the reaction, preferably until the reaction has gone to completion, to permit the hexa-substituted piperazine derivative and nitronium anions to react and form 4,10-dinitro-2,6,8,12-tetraoxa-4,10-diazatetracyclo-[5.5.0.0$^{5,9}$0$^{3,11}$]-dodecane. Additionally, at least one NO$_x$ scavenger is added to the medium to reduce NO$_x$ concentration. After the reaction has occurred, the medium is cooled to a sufficiently low temperature range to precipitate the 4,10-dinitro-2,6,8,12-tetraoxa-4,10-diazatetracyclo-[5.5.0.0$^{5,9}$0$^{3,11}$]-dodecane.

Preferably, the combining of the hexa-substituted derivative and the medium is performed in a jacketed reaction vessel purged with an inert gas to remove $NO_x$. Approximately four hours are required to add one kilogram of the piperazine starting material to the heated reaction mixture. The reaction mixture is herein defined as being obtained following the combination of the $NO_x$ scavenger, hexa-substituted piperazine derivative, and the concentrated acid medium.

In contrast to the known processes, the present invention utilizes an outside heat source to heat up the concentrated acid medium prior to the addition of the hexa-substituted piperazine derivative. Because the reaction is exothermic in nature and generally generates sufficient heat to sustain the temperature of the reaction, the heat source may be reduced or eliminated once the exothermic reaction has commenced while simultaneously maintaining the temperature in the desired range.

The present process can be conducted on a large manufacturing scale in which the exothermic reaction process is controllable, while directly yielding greater amounts of TEX in a high purity sufficient for use in formulating explosive compositions. These advantages are obtainable without requiring the heretofore extensive further purification or recrystallization steps.

Other objects, aspects and advantages of the invention will be apparent to those skilled in the art upon reading the specification and appended claims, which explain the principles of this invention.

DETAILED DESCRIPTION OF THE INVENTION

In the present process, TEX is prepared by addition of a predried mixture of a hexa-substituted piperazine derivative to a heated acid medium comprising at least one nitrate source and at least one strong acid.

Hexa-substituted piperazine derivatives suitable for use in the present process are represented by the following general formula (1):

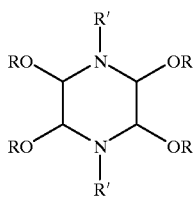

wherein —OR is a good leaving group and R is H, R", —CR"O, —COR", —COOR", —SO$_3$R", —NO, —NO$_2$, acetal (including aliphatic (e.g., formal), cycloaliphatic (e.g., cyclohexanal), and branched acetals (e.g., dimethylketal)), and cycloacetals; R' is a nitrolyzable group such as —CR"O, —COR", —SO$_2$R", —SO$_3$M, —NO$_2$, —COOR", t-butyl, cyclohexyl, and isopropyl; M is an alkali metal, preferably lithium, sodium, or potassium; R" is H, $C_1$ to $C_{10}$ alkyl, branched alkyl, cycloalkyl, and aryl (such as phenyl and substituted phenyl) and monocyclic heterocyclic moieties, and wherein each R, R', or R" can independently be the same or different. As used herein, phenyl substituents include, but are not limited to, $C_1$ to $C_{10}$ alkyl, branched alkyl, halogen, nitro, amino, substituted amino, alkoxy, acyl, and carbonyl containing moieties such as carboxyl, ester, ketone, etc. Exemplary, suitable monocyclic heterocyclic moieties contain one or more heteroatoms such as nitrogen, sulfur, and/or oxygen (e.g., triazine, thiophene, and furan). Representative hexa-substituted piperazine derivatives include, for example, 1,4-bis(methanesulphonyl)-2,3,5,6-tetrahydroxypiperazine, disodium-2,3,5,6-tetrahydroxypiperazine-1,4-disulphonate, 1,4-diformyl-2,3,5,6-tetraacetoxypiperazine, and 1,4-diformyl-2,3,5,6-tetrahydroxypiperazine (THDFP). Of the above hexa-substituted piperazine derivatives, THDFP is the preferred starting material. THDFP is illustrated below by the following formula (2):

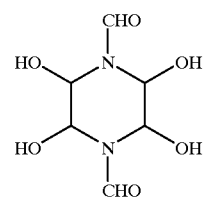

Typical hexa-substituted piperazine derivatives which may be used to synthesize TEX can be prepared by reacting glyoxal with an amide, sulfonamide, or sulfonate salt in known methods. Other hexa-substituted piperazine derivatives which may be used in the present invention are reported in Currie, A. C., et al., "Base-catalysed Reactions of Glyoxal. Part I. 1,4-Diformyl- and 1,4-Bismethylsulphonyl-Derivatives of 2,3,5,6-tetrahydroxypiperazines," *Journal of the Chemical Society* (Sect. C), pp. 491–496 (1967) and Dinwoodie, A. H. et al, "Base-catalysed Reactions of Glyoxal. Part II. 2,3,5,6-Tetrahydroxypiperazine-1,4-disulphonic Acid Derivatives," *Journal of the Chemical Society* (Sect. C), pp. 496–497 (1967).

As used herein, hexa-substituted piperazine derivatives, and more particularly diacyltetraoxypiperazine derivatives also include TEX intermediate products, such as tetraoxa-diazaisowurtzitane derivatives which may be prepared from diacyltetraoxypiperazine derivatives.

By preference, the present process also includes several features to reduce the amount of water present in the reaction mixture. The presence of water in the reaction mixture can affect the overall reaction by (a) increasing the $NO_x$ produced which increases reaction instability, and (b) decreasing the nitrating strength of the acid which, in turn, decreases yield of TEX.

The hexa-substituted piperazine derivative and $NO_x$ ingredient can be can be subject to a pre-drying treatment prior to addition to the acid medium to obtain, by preference, a finely ground homogenous composition. The pre-mix can be a fine ground and blended product, i.e., a homogenous pulverulent composition. Suitable drying conditions include, for example, overnight drying or drying for about 24 hours under vacuum, typically about 10 mm Hg, at about 50° C. to about 60° C. The upper temperature is limited by the decomposition temperature of the reactants, although the upper temperature can be on the order of about 150° C. This predrying process removes residual water from these materials. As stated above, the predrying treatment results in an increased TEX yield.

The reaction vessel is optionally purged with an inert gas, and the hexa-substituted piperazine derivative is added to the medium while the medium is heated in a range of from 55° C. to about 70° C., more preferably 55° C. to about 60° C. Approximately four hours are required to add one kilogram of the piperazine starting material to the heated medium. The temperature is maintained between 55° C. to about 70° C., more preferably between 55° C. and bout 65° C., throughout the addition of the piperazine starting material to the acid medium, and preferably until the reaction has gone to completion. If the reaction is conducted at too low a temperature, for example, below about 55° C., then the formation of undesired side products is increased and yield of TEX is decreased. In contrast, too high a reaction temperature, for example, above about 70° C., results in increased reaction instability and likelihood of fume-off, increased $NO_x$ production, and lower TEX yield.

Known preparative methods control the exothermic nature of the TEX synthesizing reaction by initial cooling of the acid medium so that the only heat supplied to the bath was heat generated by the exothermic reaction. Although not being bond by any theory, it is believed that in the known methods the primary reason why complete conversion of the hexa-substitute piperazine derivative to TEX is not achieved is because the reaction medium is not at a sufficiently high temperature during the initial stage of the reaction to support the reaction during the addition of the initial portions of the hexa-substituted piperazine derivative to the acid medium. Thus, it is not until the addition of later portions of the piperazine starting material that the medium reaches a sufficient temperature to support the reaction to an acceptable degree. By contrast, in the present process the initial heating of the acid medium permits the first added portion of the hexa-substituted piperazine derivative to more completely react.

Suitable nitronium ion sources include nitric acid and/or ammonium nitrate. The preferred nitronium ion source is 90% concentrated nitric acid. Representative strong acids that may be used with the nitronium ion source for generating nitronium anions include inorganic acids, such as sulfuric acid, oleum, nitric acid, or hydrohalo acids, such as, hydrochloric acid. Organic acids and anhydrides thereof, such as, trifluoroacetic acid (TFA), and trifluoroacetic anhydride (TFAA), are also suitable for use in the present invention. Preferably, the strong acid is highly concentrated nitric acid or sulfuric acid.

Generally, the ratio of strong acid to nitronium anion source can be from about 1:2 to about 1:20. The acid medium preferably comprises sulfuric acid mixed in combination with the preferred nitrate source of 90% concentrated nitric acid. This acid medium may contain up to about 40% concentrated sulfuric acid by volume, 35–50% of the sulfuric acid present in the acid medium may comprise oleum. The oleum may contain from about 15 wt % to about 30 wt % $SO_3$. Without being bound thereby, it is postulated that the oleum scavenges moisture from the reaction mixture and its use results in a higher purity TEX product.

The overall reaction can produce significant quantities of $NO_x$. An uncontrollable reaction condition can result if the production of $NO_x$ becomes too rapid. Addition of one or more $NO_x$ scavenger(s) can reduce the amount of $NO_x$ present and result in a more mild, controllable reaction process. Representative $NO_x$ scavengers suitable for use in the present process include, among others, sulfamic acid, sulfamide, urea, and urea derivatives. Suitable urea derivatives include alkylated ureas, such as, 1,1'-dialkylurea or N,N'-dialkylurea, in which the alkyls may be chosen independently from one another and preferably are lower alkyls having less than six carbon atoms, of which methyl and ethyl are illustrative. The amount added is sufficient to scavenge $NO_x$, and, when added, may, in general, be greater than 0 wt. % to about 10 wt. %, such that the reaction mixture does not fume off or become unstable.

Additionally, purging of the reaction vessel with an inert gas, such as nitrogen or argon, can remove excess $NO_x$. Preferably, urea is the $NO_x$ scavenger and is added to the piperazine-derivative starting material prior to the predrying process. Typically, addition of more than 0 wt. % up to about 25 wt. % of urea efficiently controls $NO_x$ production. Preferably, no more than about 10 wt. % urea is added to the piperazine derivative. Excessive amounts of urea can lead to by-product formation and decrease yield of TEX.

The reaction product is precipitated by cooling, such as in an ice bath, followed by filtering and purifying. Currently preferred purification techniques include heating the reaction product in nitric acid, washing with methanol, and/or washing with a base to neutralize excess acid. Crystal size of the reaction product can be controlled by the cooling rate of the reaction mixture. Thus, to obtain larger size crystals it is preferable to allow the reaction mixture to slowly cool to ambident temperature prior to filtering off the precipitated product and drying.

The pure product may be obtained by suitable separation techniques, such as crystallization or recrystallization techniques known to those skilled in the art. Typical crystallization solvents which may be used include acetonitrile, acetone, butyrolacetone, nitric acid, ethyl acetate, pyridine, DMSO, and DMF.

Typically, TEX yields are greater than 20% by weight based on the amount of piperazine starting material, and the purity is typically 99.8% or greater based on proton NMR analysis.

Optionally, an inert co-solvent may also be added to the acid medium prior to heating. The inert co-solvent acts as a thermal diluent and heat transfer agent by absorbing the heat generated by the exothermic reaction, boiling, and transferring the heat to a reflux condenser. The inert co-solvent further reduces the intensity of the exotherm and the probability of an uncontrollable reaction. Suitable inert co-solvents include organic solvents which do not react substantially with the reaction components under acidic reaction conditions. Representative inert co-solvents include 1,2-dichloroethane, methylene chloride, and tetramethylene sulfone (sulfolane).

The TEX as obtained can be utilized in explosive compositions. The use of TEX in explosive compositions is discussed in greater detail in U.S. Pat. No. 5,529,649, the complete disclosure of which is incorporated herein by reference. TEX may be used alone or in combination with conventional or novel solid explosive ingredients as the basis for formulating very high performance insensitive explosive compositions, such as taught in U.S. Pat. No. 5,587,553, the complete disclosure of which is incorporated herein by reference. For example, TEX may be used in combination with at least one binder, metal, and oxidizer, and optionally other explosive compounds to prepare low cost, castable explosives. Typical formulations may contain from about 5 wt % to about 90 wt % TEX, preferably from about 30 wt % to about 90 wt % TEX; from about 10 wt % to about 30 wt % binder; from about 0 wt % to about 50 wt % oxidizer; and from about 0 wt % to about 30 wt % reactive metal.

Representative inert polymeric binders include HTPB (hydroxy-terminated polybutadiene), PBAN (butadiene-acrylonitrile-acrylic acid terpolymer), PPG (polypropylene glycol), PEG (polyethylene glycol), polyesters, polyacrylates, polymethacrylates, CAB (cellulose acetate butyrate), or mixtures thereof. Representative energetic polymeric binders include PGN (polyglycidyl nitrate), poly-NMMO (nitratomethyl-methyloxetane), GAP (polyglycidyl azide), 9DT-NIDA (diethyleneglycol-triethyleneglycol-nitraminodiacetic acid terpolymer), poly-BAMO (poly(bisazidomethyloxetane)), poly-AMMO (poly(azidomethyl-methyloxetane)), poly-NAMMO (poly(nitraminomethylmethyloxetane)), copoly-BAMO/NMMO, BAMO/AMMO, nitrocellulose, or mixtures thereof. The binder can optionally be halogenated, such as fluorinated ethylene propylene copolymer, chlorotrifluoroethylene and vinylidene fluoride copolymer, polyvinylidene fluoride, polydifluorochloroethylene, fluorinated polyethers, PVC, polytetrafluoroethylene, or mixtures thereof.

Representative oxidizers include AP (ammonium perchlorate), AN (ammonium nitrate), HAN (hydroxylammonium nitrate), AND (ammonium dinitramide), or mixtures thereof.

Representative reactive metals include aluminum, magnesium, boron, titanium, zirconium, or mixtures thereof.

Other explosives that can be used in combination with TEX include RDX (1,3,5-trinitro-1,3,5-triaza-cyclohexane), HMX (1,3,5,7-tetranitro-1,3,5,7-tetraaza-cyclooctane), NTO (3-nitro-1,2,4-triazol-5-one), NQ (nitroguanidine), HNIW (2,4,6,8,10,12-hexanitro-2,4,6,8,10,12-hexaazatetracyclop[5.5.0.0$^{5,9}$0$^{3,11}$]dodecane), TATB (1,3,5-triamino-2,4,6-trinitrobenzene), and DADNE (1,1-diamino-2,2-dinitro ethane).

TEX and a small amount of binder may also be used to prepare high solids (>90% TEX) pressable or extrudable explosives. The pressable or extrudable explosives have a high solids content and contain up to about 98.5 wt % TEX, preferably from 50 wt % to 98.5 wt % TEX, and most preferably from 80 wt % to 98.5 wt % TEX, or a combination of TEX and other explosive. The pressable or extrudable explosives can also contain inert and/or energetic plasticizers. Representative inert plasticizers include DOA (dioctyladipate), IDP (isodecylperlargonate), DOP (dioctylphthalate), DOM (dioctylmaleate), DBP (dibutylphthalate), oleyl nitrile, or mixtures thereof. Representative energetic plasticizers include BDNPF/BDNPA (bis(2,2-dinitropropyl)acetal/bis(2,2-dinitropropyl)formal), TMETN (trimethylolethanetrinitrate), TEGDN (triethyleneglycoldinitrate), DEGDN (diethyleneglycol-dinitrate), NG (nitroglycerine), BTTN (butanetrioltrinitrate), alkyl NENA's (nitratoethylnitramine), or mixtures thereof.

Melt cast explosives may be prepared by combining TEX with an energetic or inert material having a relatively low melt temperature (<120° C.). Representative meltable energetic materials include TNT (2,4,6-trinitrotouene) and TNAZ (1,3,3-trinitroazetidine). Other meltable energetic materials which may be used include AN/NQ eutectic or alkylammonium nitrate salts. Inert meltable materials such as polyethylene and hydrocarbon wax may also be used. The melt cast explosives may also contain a metal, oxidizer and other nitramine.

The following examples are offered to further elaborate on the synthesis method of the present invention. These examples are intended to be exemplary and should not be viewed as exhaustive or exclusive as to the scope of the invention.

EXAMPLES

PRETREATMENT OF THDFP

In the examples where a THDFP/urea mixture is used, the mixture is prepared by blending THDFP, which has been ground into a fine powder with no particles greater than about 1 mm diameter, and urea together and then drying overnight under vacuo at 50° C. to 60° C., so as to obtain an at least essentially homogenous physical blend of fine particles. The mixture is then cooled to room temperature prior to use.

Comparative Example A—Preparation according to U.S. Pat. No. 5,498,711

To a water cooled, vigorously stirred solution of 390 ml white fuming nitric acid and 250 ml concentrated sulfuric acid in a 4 liter Erlenmeyer flask was added a mixture of 206 g (1.0 mole) of THDFP and 33 g (0.55 mole) urea, portionwise such that the temperature did not exceed 50° C. Upon completion of the addition, the water bath was removed and the temperature rose to 65° C. The mixture was then allowed to cool to below about 30° C. at which point the entire contents of the flask were poured on ice and the solid precipitate was collected on a glass frit.

The solid was washed sequentially with water, saturated sodium bicarbonate, water again, and finally methanol. The product was died in vacuo at 60° C. overnight.

TEX produced in this manner can be further purified by dissolution and heating in hot (80° C.) nitric acid for eight hours, cooling to room temperature, and pouring over ice. The solid precipitate can be collected, washed with water, sodium bicarbonate and more water. The final dried product is analytically pure TEX with an Acid Number (AN) of less than 0.05 mg base/g product.

The Acid Number is the amount of base, for instance, KOH or NaOH, needed to neutralize 1 g of material. TEX preferably has an Acid Number of less than 0.05 mg/g in order to be used in formulating explosive compositions.

Example 1

A 12 liter jacketed three-necked flask was equipped with a stirring apparatus, the 2 outer necks were equipped with condensers and either a thermometer or nitrogen purge, respectively.

The three-necked flask was charged with 675 ml of $H_2SO_4$ followed by 675 ml of fuming $H_2SO_4$ (20% $SO_3$). The nitrogen purge and stirring apparatus were started. The vessel was then charged with 2250 ml of 90% $HNO_3$. The temperature of the mixture increased to 60° C. A predried mixture of 618 grams of THDFP and 92 grams of urea was then added slowly to the pot over 7 hours, in portions of about 30 grams at a time. A reaction mixture temperature between 55–60° C. was maintained during the addition of the THDFP/urea mixture. Stirring and nitrogen purge were continued after the final addition of the THDFP/urea mixture. The reaction mixture gradually cooled to around 40° C. The entire contents of the reaction container were then poured over ice and the solid precipitate was collected on a glass frit.

The white solid was then washed 3 times with two liters of distilled water, two liters of acetone, and then collected and dried under vacuum at 60° C. The final yield was 165.6 grams of TEX with an Acid Number of less than 0.05 mg/g.

Example 2

TEX was prepared according to the procedure of Example 1, except that 30% $SO_3$ fuming $H_2SO_4$ was used. A total of 168.4 grams of TEX with an Acid Number of less than 0.05 mg/g was collected.

Example 3

TEX was prepared according to the procedure of Example 1, except that the procedure was carried out using 30% $SO_3$ fuming $H_2SO_4$ and the THDFP/urea mixture was dried for 48 hours at 60° C. prior to addition to the acid mixture. The yield of the final product was 166.7 grams of TEX with an Acid Number of less than 0.05 mg/g.

Purity of each of the Examples was determined by proton NMR to determine the amount of monoformyl substituent impurity substituted for the nitro groups at the 4 and 10 ring positions. Generally, purity levels were found to be 97 wt % or greater, compared to a purity of about 60 wt % to 70 wt % in the prior art.

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. The foregoing detailed description is not intended to be exhaustive or to restrict the invention to the precise embodiments disclosed. Modifications and equivalents will be apparent to practitioners skilled in this art and are encompassed within the spirit and scope of the appended claims.

What is claimed is:

1. A process for synthesizing 4,10-dinitro-2,6,8,12-tetraoxa-4,10-diazatetracyclo-[5.5.0.0$^{5,9}$0$^{3,11}$]-dodecane, comprising:
   (a) combining at least one hexa-substituted piperazine derivative with a medium, said medium being in a range from about 55° C. to about 70° C. in temperature and comprising at least one nitronium anion source and at least one acid sufficiently strong to generate nitronium anions from the nitronium anion source, and maintaining the medium from about 55° C. to about 70° C. to permit the hexa-substituted piperazine derivative and nitronium anions to react and form 4,10-dinitro-2,6,8,12-tetraoxa-4,10-diazatetracyclo-[5.5.0.0$^{5,9}$0$^{3,11}$]-dodecane;
   (b) combining the medium with at least one NO$_x$ scavenger; and
   (c) subsequent to said (a) combining of the hexa-substituted piperazine-derivative with the medium, cooling the medium into a sufficiently low temperature range to precipitate the 4,10-dinitro-2,6,8,12-tetraoxa-4,10-diazatetracyclo-[5.5.0.0$^{5,9}$0$^{3,11}$]-dodecane.

2. The process of claim 1, wherein said (c) cooling of the medium is performed subsequent to completion of the formation of the 4,10-dinitro-2,6,8,12-tetraoxa-4,10-diazatetracyclo-[5.5.0.0$^{5,9}$0$^{3,11}$]-dodecane.

3. The process of claim 1, wherein in said (a) combining of the hexa-substituted piperazine derivative with the medium, the medium is maintained in a range of from about is 55° C. to about 65° C.

4. The process of claim 1, wherein in said (a) combining of the hexa-substituted piperazine derivative with the medium, the medium is in a range of from about 55° C. to about 60° C. at the time the hexa-substituted piperazine derivative is combined with the medium.

5. The process of claim 1, wherein said (b) combining of the medium of the NO$_x$ scavenger is performed prior to said (a) combining of the hexa-substituted piperazine derivative with the medium.

6. The process of claim 1, further comprising combining the medium with at least one co-solvent.

7. The process of claim 6, wherein the co-solvent comprises at least one member selected from the group consisting of 1,2-dichloroethane, methylene chloride, and tetramethylene sulfone.

8. The process of claim 1, wherein the NO$_x$ scavenger comprises at least one member selected from the group consisting of sulfamic acid, sulfamide, urea, and urea derivatives.

9. The process of claim 1, wherein the NO$_x$ scavenger is present in the medium in a concentration not greater than about 10 wt %.

10. The process of claim 1, wherein the acid comprises an inorganic acid.

11. The process of claim 10, wherein the organic acid comprises at least one member selected from the group consisting of sulfuric acid, nitric acid, and hydrohalo acids.

12. The process of claim 1, wherein the acid comprises at least one member selected from the group consisting of organic acid and anhydrides thereof.

13. The process of claim 12, wherein the acid comprises at least one member selected from the group consisting of trifluoroacetic acid and trifluoroacetic acid.

14. The process of claim 1, wherein the nitronium anion source comprises at least one member selected from the group consisting of nitric acid and ammonium nitrate.

15. A process for synthesizing 4,10-dinitro-2,6,8,12-tetraoxa-4,10-diazatetracyclo-[5.5.0.0$^{5,9}$0$^{3,11}$]-dodecane, comprising:
   (a) combining at least one hexa-substituted piperazine derivative with a medium, said medium being in a range from about 55° C. to about 70° C. in temperature and comprising sulfuric acid and at least one member selected from the group consisting of nitric acid and ammonium nitrate, and maintaining the medium from about 55° C. to about 70° C. to permit the hexa-substituted piperazine derivative and nitronium anions to react and form 4,10-dinitro-2,6,8,12-tetraoxa-4,10-diazatetracyclo-[5.5.0.0$^{5,9}$0$^{3,11}$]-dodecane;
   (b) combining the medium with at least one NO$_x$ scavenger; and
   (c) subsequent to said (a) combining of the hexa-substituted piperazine-derivative with the medium, cooling the medium into a sufficiently low temperature range to precipitate the 4,10-dinitro-2,6,8,12-tetraoxa-4,10-diazatetracyclo-[5.5.0.0$^{5,9}$0$^{3,11}$]-dodecane.

16. The process of claim 15, wherein said (c) cooling of the medium is performed subsequent to formation of the 4,10-dinitro-2,6,8,12-tetraoxa-4,10-diazatetracyclo-[5.5.0.0$^{5,9}$0$^{3,11}$]-dodecane.

17. The process of claim 15, wherein in said (a) combining of the hexa-substituted piperazine derivative with the medium, the medium is maintained in a range of from about is 55° C. to about 65° C.

18. The process of claim 15, wherein in said (a) combining of the hexa-substituted piperazine derivative with the medium, the medium is in a range of from about 55° C. to about 60° C. in temperature at the time the hexa-substituted piperazine derivative is combined with the medium.

19. The process of claim 15, wherein said (b) combining of the medium of the NO$_x$ scavenger is performed prior to said (a) combining of the hexa-substituted piperazine derivative with the medium.

20. The process of claim 15, wherein the NO$_x$ scavenger comprises urea.

21. A process according to claim 1, wherein the product from said (c) is washed and dried to obtain 4,10-dinitro-2,6,8,12-tetraoxa-4,10-diazatetracyclo-[5.5.0.0$^{5,9}$0$^{3,11}$], dodecane having an acid number less than 0.05 mg/g.

* * * * *

UNITED STATES PATENT AND TRADEMARK OFFICE
CERTIFICATE OF CORRECTION

PATENT NO. : 6,107,483
DATED : August 22, 2000
INVENTOR(S) : Robert B. Wardle, Robert M. Hajik, Jerald C. Hinshaw and Thomas K. Highsmith Page 1 of 1

It is certified that error appears in the above-identified patent and that said Letters Patent is hereby corrected as shown below:

Title page,
ABSTRACT, change "anion" to -- ion --; change "anions" to -- ions --.

Column 2,
Lines 49 and 51, change "anion" to -- ion --;
Lines 50 and 58, change "anions" to -- ions --.

Column 5,
Line 30, change "anions" to -- ions --;
Line 37, change "anion" to -- ion --.

Column 9,
Lines 23 and 25, change "anion" to -- ion --;
Lines 25 and 28, change "anions" to -- ions --.

Column 10,
Line 15, change "anion" to -- ion --;
Line 28, change "anions" to -- ions --.

Signed and Sealed this

Thirtieth Day of April, 2002

Attest:

*Attesting Officer*

JAMES E. ROGAN
*Director of the United States Patent and Trademark Office*